United States Patent [19]

Kawasaki et al.

[11] Patent Number: 5,278,288
[45] Date of Patent: Jan. 11, 1994

[54] PROCESS FOR PRODUCING κ-CASEIN GLYCOMACROPEPTIDES

[75] Inventors: Yoshihiro Kawasaki, Kawagoe; Shunichi Dosako, Urawa, both of Japan

[73] Assignee: Snow Brand Milk Products Co., Ltd., Hokkaido, Japan

[21] Appl. No.: 798,482

[22] Filed: Nov. 26, 1991

[30] Foreign Application Priority Data

Nov. 29, 1990 [JP] Japan .................................. 2-325166

[51] Int. Cl.$^5$ .......................... C07K 1/00; C07K 15/14
[52] U.S. Cl. .................... 530/361; 530/395; 530/322; 435/68.1
[58] Field of Search ...................... 530/361, 322, 395; 435/68.1

[56] References Cited

U.S. PATENT DOCUMENTS

| | | | |
|---|---|---|---|
| 4,042,576 | 8/1977 | Eustache | 530/322 |
| 5,061,622 | 10/1991 | Dosako et al. | 435/68.1 |
| 5,075,424 | 12/1991 | Tanimoto et al. | 530/361 |

Primary Examiner—Howard E. Schain
Assistant Examiner—P. Lynn Touzeau
Attorney, Agent, or Firm—Browdy and Neimark

[57] ABSTRACT

The present invention provides a process for producing a κ-casein glycomacropeptide comprising contacting milk raw materials containing the κ-casein glycomacropeptide with an ion exchanger; collecting a fraction which does not adsorb on the ion exchanger; and concentrating and desalting the fraction to obtain the κ-casein glycomacropeptide.

11 Claims, No Drawings

PROCESS FOR PRODUCING κ-CASEIN GLYCOMACROPEPTIDES

BACKGROUND OF THE INVENTION

The present invention relates to a process for the simple production of κ-casein glycomacropeptides having useful physiological activities.

FIELD OF INVENTION

It is known that κ-casein glycomacropeptides are peptides bonded to sialic acid which are produced by a reaction of κ-casein of cow milk and rennet or pepsin and they are present in cheese whey.

Hitherto, some methods were reported for the production of κ-casein glycomacropeptides, for example, a method comprising dissolving κ-casein which is isolated from cow's milk in deionized water, reacting the obtained solution with pepsin, adding trichloroacetic acid to the solution to precipitate a para-κ-casein fraction, dialyzing the obtained supernatant against deionized water for desalting, and freeze-drying the obtained solution (Stan et al., Bulletin of Experimental Biology and Medicine, 96, 889 (1983)); and a method comprising dissolving the above κ-casein in deionized water, adjusting the pH of the solution to 6.7, reacting the solution with rennet, readjusting the pH to 4.6 to precipitate the para-κ-casein, removing the precipitate, dialyzing the obtained supernatant for desalting, and freeze-drying the obtained solution (Published by Academic Press Company, "Milk Protein", pp 200).

However, these methods are conducted in laboratories and are not suitable for mass production.

On the other hand, since the industrial utilization of κ-casein glycomacropeptides has been previously unknown, a method for mass producing the compounds has not been studied.

Since it was reported that after taking κ-casein glycomacropeptides dogs lost their appetite (Bulletin of Experimental Biology and Medicine, 96, 889, (1983)), it has been found that the compounds can be utilized as food materials for the prevention of obesity. Further, since it was found that κ-casein glycomacropeptides were effective to prevent the adhesion of E. coli to cells of the intestines, to protect the infection of influenza virus (Japanese Patent Unexamined Publication No. 63-284133) or to protect the adhesion of tartar to teeth (Japanese Patent Unexamined Publication No. 63-233911), the demand for the production of κ-casein glycomacropeptides on a large industrial scale is expected.

Given such conditions, a process for preparing a κ-casein glycomacropeptide from rennet casein curd whey has been reported (Japanese Patent Unexamined Publication No. 63-284199). Since the reaction of the process may proceed without the trichloroacetic acid of the prior art, the process can be utilized in food fields and in mass-production. However, the method can not be used with the rennet casein curds which are obtained as a by-product of the rennet casein curd whey. If the rennet casein curds are not utilized, the production cost of κ-casein glycomacropeptides becomes prohibitively expensive.

The inventors of the present invention found that the molecular weight of κ-casein glycomacropeptide changes sharply at pH 4. Using the property, they found a process for producing the κ-casein glycomacropeptide at a moderate price (Japanese Patent Unexamined Publication No. 2-276542).

The process for the production of κ-casein glycomacropeptides comprises adjusting the pH to below 4 of a solution of milk starting materials such as cheese whey, whey protein concentrate and cheese whey from which protein has been removed, treating the solution by ultrafiltration with a membrane having a molecular weight cut-off of 10,000–50,000 to obtain the filtrate of the solution, preferably readjusting the pH of the filtrate to 4 or higher, and concentrating the obtained filtrate with a membrane having a molecular weight cut-off of 50,000 or less to obtain the desalted concentrate.

According to the above invention, the pH value of the solution of milk starting materials such as cheese whey, whey protein concentrate and cheese whey from which protein has been removed is adjusted. Such a simple operation can provide a process for producing κ-casein glycomacropeptides on a large scale and at a low cost. The obtained product has high purity.

Moreover, in a factory where the whey protein concentrate has been produced, new equipment is not required because κ-casein glycomacropeptides can be produced with an ultrafilter or a reverse osmosis hyperfilter used for preparing the whey protein concentrate. The protein fraction from which the κ-casein glycomacropeptides have been removed can be used as the whey protein concentrate.

However, to lower the production cost of κ-casein glycomacropeptides, the whey protein concentrate should be prepared by desalting and drying after neutralizing the whey protein which is a by-product in the process. Further, when the κ-casein glycomacropeptides are recovered from the whey concentrate obtained by ultrafiltration, the permeation flux is lowered by protein fouling. As a result, the problem is the necessity of long time operation.

In addition, a method for the mass production of a κ-casein glycomacropeptide is disclosed in Japanese Patent Application No. 2-95686. The method comprises heating a solution containing whey protein, freezing the solution, defrosting the frozen solution, concentrating the obtained supernatant to obtain the desalted concentrate of the κ-casein glycomacropeptide. The cost and the operation time are improved by the method, but the purity of the κ-casein glycomacropeptide is not increased.

SUMMARY OF THE INVENTION

An object of the present invention is to provide a process for the mass production of κ-casein glycomacropeptides advantageous to the purity, the cost and the operation time. Further, the inventors of the present invention have found that when materials isolated from whey proteins are prepared with a cation-exchange resin, main whey proteins adsorb on the resin and a filtrate fraction is obtained which is rich in κ-casein glycomacropeptides. Accordingly, the object of the present invention is to provide a process for preparing κ-casein glycomacropeptides from the fraction.

The present invention provides a process for producing a κ-casein glycomacropeptide, characterized in that it comprises contacting milk raw materials containing the κ-casein glycomacropeptide with a cation exchanger; collecting a fraction which does not adsorb on the cation exchanger; and concentrating and desalting the fraction to obtain the κ-casein glycomacropeptide.

In said concentrating and desalting step, preferably, the pH value of the fraction which does not adsorb on the cation exchanger is adjusted to below 4, the adjusted fraction is treated by ultrafiltration treatment with a membrane having a molecular weight cut-off of 10,000 to 50,000, and the obtained filtrate is treated with a membrane having a molecular weight cut-off of 50,000 or less.

Further preferably, the pH value of the filtrate obtained by ultrafiltration is readjusted to 4 or higher.

It is preferred to use a membrane having a molecular weight cut-off of 10,000 or less for the filtrate.

In the preparation of tag materials isolated from whey proteins with a cation exchange resin, main whey proteins adsorbing on the resin and a filtrate fraction containing κ-casein glycomacropeptides are separated. The filtrate fraction may be concentrated, desalted and dried as it is. Pure compounds can be obtained by a process described in Japanese Patent Application No. 1-97583. Namely, the pH value of the filtrate fraction is adjusted to pH 4 or lower, the fraction is treated with a membrane having a molecular cut-off of 10,000 to 50,000, the pH value of the obtained filtrate is readjusted to pH 4 or higher, and the filtrate is concentrated, desalted and dried to obtain κ-casein glycomacropeptide.

According to the process of the present invention, the is minimal fouling of whey proteins during the ultrafiltration. Permeation flux of the filtrate is increased. As a result, κ-casein glycomacropeptides having a high purity are obtained by short time operation.

The following describes in detail the process for preparing κ-casein glycomacropeptides of the present invention.

DETAILED DESCRIPTION OF THE INVENTION

Technique for the adsorption of whey proteins on an ion exchanger has been previously known; J. N. de Wit et al., Neth. Milk Dairy J., 40, 41–56 (1986), J. S. Ayers et al., New Zealand J. Dairy Sci. and Tech., 21, 21–35 (1986), Japanese Patent Unexamined Publication No. 52-151200 and Japanese patent Unexamined Publication No. 2-104246.

Any kind of milk raw materials containing κ-casein glycomacropeptides may be used. Cheese whey, whey protein concentrate which is produced by ultrafiltration, cheese whey from which a whey protein precipitate has been removed by heat treatment, and lactose mother liquor may be exemplified.

When the whey protein concentrate is used, it is diluted with water. The concentration is not limited. Any kind of cheese whey can be used. Since small quantities of casein curds and fatty contents remain in the cheese whey, they are removed with a centrifuge, a cream separator or a clarifier prior to use. Lactose principally contained in the cheese whey from which protein has been removed by heating, is precipitated by the treatment. The precipitated lactose is removed with a centrifuge, a clarifier or by decantation.

Then, the pH value of the raw materials is adjusted according to cation exchangers. For example, when a cation exchanger having carboxy methyl groups for exchange groups is used, the pH value is adjusted to 3–4.5. When a cation exchanger having diethyl amino groups for exchange groups is used, the pH value is adjusted to 6–7. The pH adjustment can be achieved using an acid or an alkali. For such an acid, hydrochloric acid, sulfuric acid, acetic acid, lactic acid and citric acid may be exemplified. For such an alkali, sodium hydroxide, sodium bicarbonate and ammonia may be exemplified. For other cation exchangers, a cation exchanger having sulfone groups or quaternary amine groups may be exemplified. A method for adsorbing whey proteins containing in materials on a cation exchanger is achieved using said conventional methods and separating into a fraction containing compounds adsorbed on a cation exchanger and a fraction containing compounds not adsorbed on the cation exchanger.

Moreover, in the step of contacting a resin with raw materials, a rotating column disclosed in Japanese Patent Unexamined Publication No. 2-138295 is preferably used to treat efficiently the materials in a large scale.

The non-adsorbed fraction thus obtained may be concentrated and desalted. The monomer of κ-casein glycomacropeptides (molecular weight 9,000) is obtained at the pH value 4 or lower and the polymer of κ-casein glycomacropeptides (molecular weight 45,000–50,000) is obtained at the pH value above 4. In the step of concentrating and desalting a solution by ultrafiltration, when the pH value of the solution is 4 or lower, a membrane having a molecular weight cut-off of 10,000 or less should be used.

When highly pure κ-casein glycomacropeptides are required, the pH value of said non-adsorbed fraction is adjusted to 4 or lower, preferably to $3\pm0.5$. When the pH value is 4 or higher, the molecules of the κ-casein glycomacropeptide are associated, the molecular weight becomes greater and these molecules pass through the membrane only with difficulty. The lower limit of the pH value is not particularly limited. When the pH value is 2.5 or lower, sialic acid which is bonded to the κ-casein glycomacropeptide becomes unstable, so that the physiological effectiveness of the compound is lowered. However, when a κ-casein glycomacropeptide having no sialic acid is required, the pH value may be 2.5 or lower. The pH adjustment can be achieved using an acid such as hydrochloric acid, sulfuric acid, acetic acid, lactic acid and citric acid or an alkali such as sodium hydroxide, sodium bicarbonate and ammonia. After adjusting the pH value, the solution is ultrafiltered. The molecular weight cut-off of the membrane used in the ultrafiltration step is 10,000 to 50,000. When a membrane having a molecular weight cut-off of below 10,000 is used, the molecules of the κ-casein glycomacropeptide are difficult to pass through the membrane. When a membrane having a molecular weight cutoff of above 50,000 is used, the molecules of the κ-casein glycomacropeptide can pass through the membrane and a part of the coexisting whey protein can also pass through the membrane, so that the purity of the κ-casein glycomacropeptide is decreased. Usually, in the production process of whey protein concentrate, the whey protein is ultrafiltered with a module equipped with a membrane having a molecular weight cut-off of about 20,000. In the process of the present invention, the above membrane can be used.

In the ultrafiltration step, the solution is preferably concentrated up to the limit and thus an improved yield rate of the filtrate is achieved. It is also preferred that water is added to the concentrated solution and the ultrafiltration is conducted, repeatedly. For increasing the permeate flow of the filtrate, the solution may be heated to about 50° C. However, When the temperature is above 60° C., the whey protein is precipitated or gels, so that the solution is preferably heated to 60° C. or less.

The obtained concentrate is dried after adjusting the pH value to neutral to obtain the powder of whey protein concentrate.

The filtrate obtained by a such process contains the κ-casein glycomacropeptide, lactose and minerals. Since the concentration of the κ-casein glycomacropeptide is lowered, the filtrate should be desalted and concentrated. The two methods of desalting and concentrating are as follows. In the first method, after adjusting the pH of the filtrate to 4 or higher, the filtrate is filtered with a membrane having a molecular weight cut-off of 50,000 or less by ultrafiltration, diafiltration or reverse osmosis hyperfiltration. The pH of the filtrate can be adjusted by an alkali such as sodium hydroxide, sodium bicarbonate and ammonia water. The monomer of the κ-casein glycomacropeptide (molecular weight 9,000) is obtained at the pH value of 4 or lower, and the polymer of the κ-casein glycomacropeptide (molecular weight 45,000) is obtained at the pH value of above 4. If desired, the pH value is adjusted to 5 or higher. Further, any membrane having a molecular weight cut-off of 50,000 or less may be used. When a membrane having a molecular weight cut-off of above 50,000 is used, the κ-casein glycomacropeptide passes through the membrane. A membrane having a molecular weight cut-off of about 20,000 which is used in the usual process of producing the concentrate of whey protein can be conveniently used.

When the pH of the filtrate is not readjusted to 4 or higher, the κ-casein glycomacropeptide exists in the monomer form. Then, the second method is used. In this method, the concentrate is obtained by means of a membrane having a fraction molecular weight of 10,000 or less, preferably 8,000 or less by ultrafiltration, diafiltration or reverse osmosis hyperfiltration.

These methods can be combined with a desalting process, e.g. by means of electrodialysis or by using an ion exchange resin.

Since the obtained concentrate substantially contains only the κ-casein glycomacropeptide, it can be dried by spray drying or freeze-drying. Furthermore, since the κ-casein glycomacropeptide is stable to heat, it is preferred to add a pasteurizing or sterilizing step prior to the drying step.

As described above, according to the present invention, κ-casein glycomacropeptides can be simply produced by using a fraction not adsorbed on a cation exchanger. The fraction is a by-product in the production of materials which are isolated from whey proteins. In this case, since the raw material is a by-product, the production cost of the κ-casein glycomacropeptides from the raw materials may be lowered. Since the main whey proteins are removed by the cation exchange resin the decrease of permeation flux based on the fouling of whey protein scarcely occurs and the operation time is shortened in comparison with conventional methods. Further, the products can be obtained without using additives such as trichloroacetic acid. Accordingly, the obtained κ-casein glycomacropeptides can be used as raw materials in the fields of food and medical supplies. It is very useful in industrial fields.

DESCRIPTION OF THE PREFERRED EMBODIMENTS

The following examples illustrate the present invention more specifically.

EXAMPLE 1

The pH value of 1 0 kg of Gouda cheese whey was adjusted to 4.0 by using hydrochloric acid. 25 g of CM-Sephadex C-50 (manufactured by Pharmacia Company, Trade name) swelled in water at 40° C. was mixed with the above cheese whey. The mixture was slowly stirred for 20 hours. A fraction which had not been adsorbed was separated from the ion exchanger with a wire gauze filter for filtration. The obtained fraction 9.9 kg was collected and ultrafiltered at 50° C. with a membrane having a molecular weight cut-off of 20,000 (manufactured by DDS Company, Trade name: GR 61 pp). The concentrated solution was desalted by diafiltration and the filtrate was freeze-dried to obtain 160 mg of κ-casein glycomacropeptide powder. The purity 55% of the powder was determined by a urea-SDS electrophoresis method.

EXAMPLE 2

Using the same method as in Example 1, 9.8 Kg of a fraction which had not adsorbed on CM-Sephadex C-50 was obtained from 10 kg of Gouda cheese whey. The pH value of the fraction was adjusted to 3.0 by using hydrochloric acid. The fraction was ultrafiltered at 50° C. with an ultrafiltration membrane having a molecular weight cutoff of 20,000 and 8.9 kg of a filtrate was obtained. 25% caustic soda aqueous solution was added to the filtrate to adjust the pH value to 7.0. The mixture was concentrated with an ultrafiltration membrane having a molecular weight cut-off of 20,000 and the concentrate was desalted by diafiltration. The obtained filtrate was freeze-dried to obtain 81 Mg Of κ-casein glycomacropeptide powder. The purity 88% of the powder was determined by an urea-SDS electrophoresis method.

EXAMPLE 3

Using the same method as in Example 1, 9.8 kg of a fraction which had not adsorbed on CM-Sephadex C-50 was obtained from 10 kg of Gouda cheese whey. The pH value of the fraction was adjusted to 3.5 with hydrochloric acid. The fraction was ultrafiltered at 50° C. with an ultrafiltration membrane having a molecular weight cut-off of 20,000 and 8.9 kg of a filtrate was obtained. The filtrate was concentrated with an ultrafiltration membrane having a molecular weight cut-off of 8,000 (manufactured by DDS Company, GR 81 pp) and then it was desalted by diafiltration. The obtained filtrate was freeze-dried to obtain 90 mg of κ-casein glycomacropeptide powder. The purity 80% of the powder was determined by an urea-SDS electrophoresis method.

EXAMPLE 4

10 kg of Gouda cheese whey having a pH value of 6.4 was passed through a column filled with 25 g of DEAE Sephadex A-50 (manufactured by Pharmacia Company) which was swelled in water at 40° C., at a flow rate of 0.5 liter/hour. Then, the column was washed with water. 12 kg of whey fractions which had not adsorbed on the column was collected. The fractions were treated by using the same method as in Example 2 and 55 mg of κ-casein glycomacropeptide powder was obtained. The purity 80% of the powder was determined by an urea-SDS electrophoresis method.

EXAMPLE 5

The pH value of 10 kg of Gouda cheese whey was adjusted to 3.0 with hydrochloric acid. The whey solution was passed through a rotary column having an internal space of 2.3 liters in which 400 g of Indion S2 (manufactured by Phenix Chemical Company) swelled in water at 50° C. was charged, at a flow rate of 100 liter/hour for one hour. Then, water was passed through the column at the same flow rate for 10 minutes to wash the resin. 26 kg of the collected whey solution was treated by using the same method as in Example 2.59 mg of κ-casein glycomacropeptide powder was obtained. The purity 82% of the powder was determined by an urea-SDS electrophoresis method.

EXAMPLE 6

The pH value of 200 kg of Gouda cheese whey was adjusted to 3.3 by using hydrochloric acid. The whey solution was passed through a rotary column having an internal space of 14 liters in which 5 liters of Vistec CM (manufactured by Viscose Group Company) swelled in water at 50° C. was charged, at a flow rate of 1000 liter/hour for 4 hours. Then, water was passed through the column at the same flow rate for 3 minutes to wash the resin. 230 kg of non-adsorbed whey and washed liquid were obtained. 1M NaCl solution (pH 8.4) containing 0.2 M $Na_2HPO_4$ was passed through the rotary column at 1000 liter/hour for 5 minutes to recover adsorbed whey proteins. The recovered proteins were ultrafiltered by the use of an ultrafilter having an membrane of a molecular weight cut off of 20,000 (manufactured by DDS Company, GR 61 pp). The obtained concentrate was treated by diafiltration. After concentrating, the product was spray-dried to obtain about 2 kg of whey protein-isolated materials.

On the other hand, the pH value of the non-adsorbed fraction was adjusted to 2.0 with hydrochloric acid, and the solution was ultrafiltered and desalted by using the same method as in Example 2 to obtain 20 liters of a filtrate. The filtrate was concentrated with a rotary evaporator. 120 ml of the concentrate was spray-dried with a Pulvis minispray-GA-31 (Yamato Company) at inlet temperature of 150° C. and outlet temperature of 85° C. to obtain 17 g of κ-casein glycomacropeptide powder. The purity 79% of the powder was determined by an urea-SDS electrophoresis method.

We claim:

1. A process for producing a K-casein glycomacropeptide comprising the following steps,
   contacting milk raw materials containing the ½-casein glycomacropeptide with a cation exchanger to adsorb a fraction of said raw milk material on said ion exchanger;
   collecting a fraction which does not adsorb on the ion exchanger; and
   concentrating and desalting the collected fraction which has not been adsorbed on the cation exchanger to obtain the K-casein glycomacropeptide.

2. A process as claimed in claim 1, wherein the concentrating and desalting step includes adjusting the pH value of the fraction which does not adsorb on the ion exchanger to below 4; ultrafiltering the fraction by with a membrane having a molecular weight cut-off of 10,000 to 50,000 to obtain a filtrate; and ultrafiltering the obtained filtrate with a membrane having a molecular weight cut-off of 50,000 or less to concentrate and desalinate the κ-casein glycomacropeptide.

3. A process as claimed in claim 2, wherein the pH value of the filtrate obtained by ultrafiltration is readjusted to 4 or higher before ultrafiltering the filtrate.

4. A process as claimed in claim 2, wherein the membrane having a molecular weight cut-off of 10,000 or less is used in said step of ultrafiltering the filtrate.

5. A process as claimed in claim 1 wherein the cation exchanger is packed into a column and further comprising passing said milk raw materials through said column.

6. A process as claimed in claim 1 wherein said cation exchangers have a side group selected from the group consisting of carboxy methyl groups, diethyl amino groups and sulfone groups.

7. A process as claimed in claim 1, wherein said milk raw materials are whey or diluted whey protein concentrate.

8. A process as claimed in claim 2, wherein the pH of the fraction which does not adsorb on the cation exchanger is adjusted to a pH of 3± about 0.5.

9. A process as claimed in claim 4, wherein said ultrafiltration of the obtained filtrate is performed using a membrane having a molecular weight cut off of 8,000 or less.

10. A process as claimed in claim 2, wherein both ultrafiltration steps are performed at a temperature below about 60° C.

11. A process as claimed in claim 1, wherein at least one ultrafiltration step is performed at about 50° C.

* * * * *